United States Patent [19]
Bekanich

[11] Patent Number: 5,366,191
[45] Date of Patent: Nov. 22, 1994

[54] SUPPORT APPARATUS FOR A PATIENT INFUSION DEVICE

[76] Inventor: Joseph Bekanich, 243 Sullivan St., Exeter, Pa. 18643

[21] Appl. No.: 836,829

[22] Filed: Feb. 19, 1992

[51] Int. Cl.⁵ ............................................. F16M 11/00
[52] U.S. Cl. ................................... 248/125; 248/408; 248/558; 248/165; 248/297.2; 403/328
[58] Field of Search ..................... 248/125, 161, 295.1, 248/414, 129, 165, 542, 122, 311.3, 408, 544, 297.2, 296, 558; 403/378, 328, 324, 361, 287, 13, 14; 604/80, 245, 246

[56] References Cited

U.S. PATENT DOCUMENTS

| | | | |
|---|---|---|---|
| 755,668 | 3/1904 | Hurxthal | 248/297.2 X |
| 1,320,613 | 11/1919 | Gilcrease | 248/408 X |
| 1,797,911 | 3/1931 | Goenen et al. | 248/408 X |
| 2,117,947 | 5/1938 | de Rome et al. | 403/324 X |
| 3,170,665 | 2/1965 | Ryan | 248/311.2 |
| 3,512,832 | 5/1970 | Kage | 248/408 X |
| 4,332,378 | 6/1982 | Pryor | 248/188.7 X |
| 4,339,212 | 7/1982 | Sauber | 403/324 X |
| 4,706,368 | 11/1987 | Crissmann, III et al. | 248/122 X |
| 4,725,027 | 2/1988 | Bekanich | 248/129 X |
| 5,007,608 | 4/1991 | Carroll, Jr. | 248/297.2 |
| 5,094,418 | 3/1992 | McBarnes, Jr. et al. | 248/125 X |
| 5,135,191 | 8/1992 | Schmuhl | 248/125 |

FOREIGN PATENT DOCUMENTS 424412 2/1935 United Kingdom ................ 403/324

Primary Examiner—Karen J. Chotkowski
Attorney, Agent, or Firm—Nies, Kurz, Bergert & Tamburro

[57] ABSTRACT

Apparatus for carrying a patient infusion device, such as an intravenous-fluid-containing bag or infusion pump. The apparatus includes an infusion device carrier that has a support connector from which a coupling rod extends. The support connector and coupling rod are releasably received in a support receptacle that is carried by a mobile stretcher, an infusion device support stand, a wheelchair, a bed, or a wall mount. The coupling rod includes a throughbore to receive a transversely slidable detent carried by the support receptacle, and alignment indicia are carried on each of the support connector and the support receptacle for properly aligning the two elements to permit them to be securely connected together. The releasable support connector permits the infusion device to be transferred from one mode of carrier to another, thereby eliminating the need for a separate person to guide an infusion device support stand to accompany a patient being transported.

20 Claims, 5 Drawing Sheets

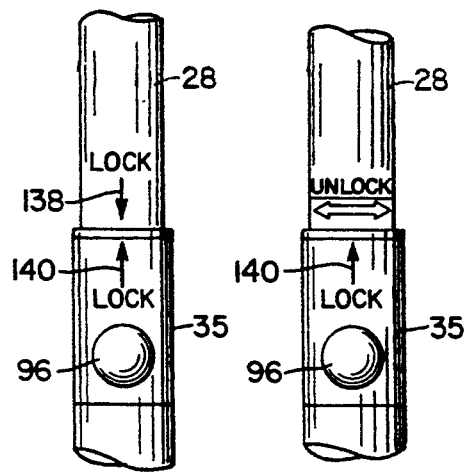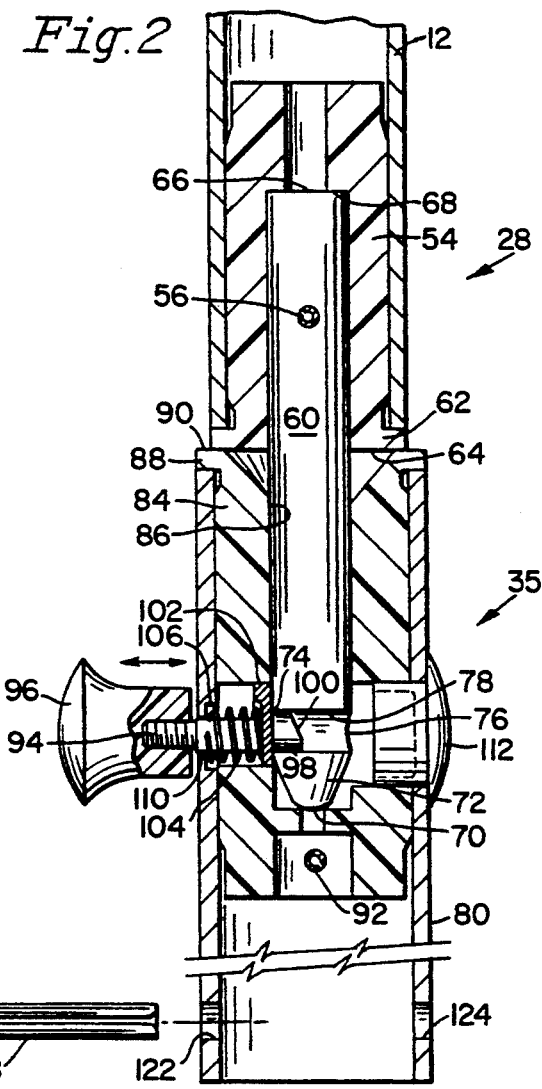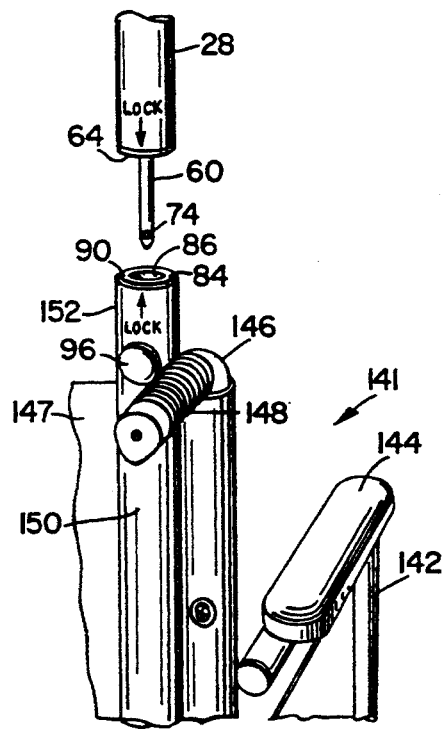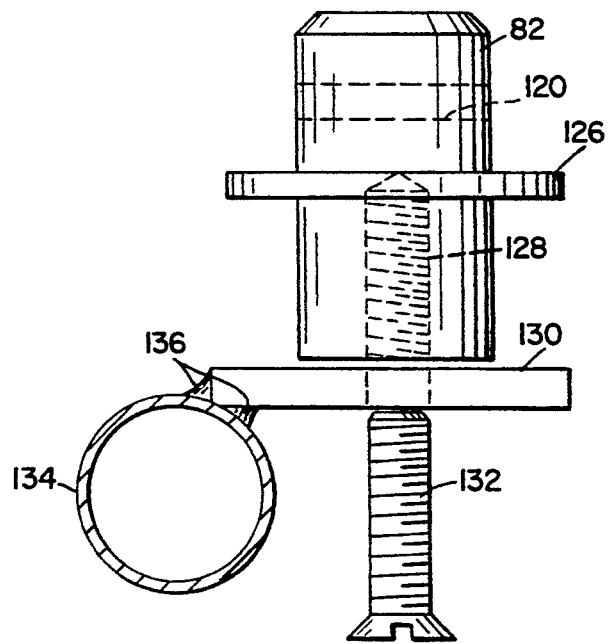

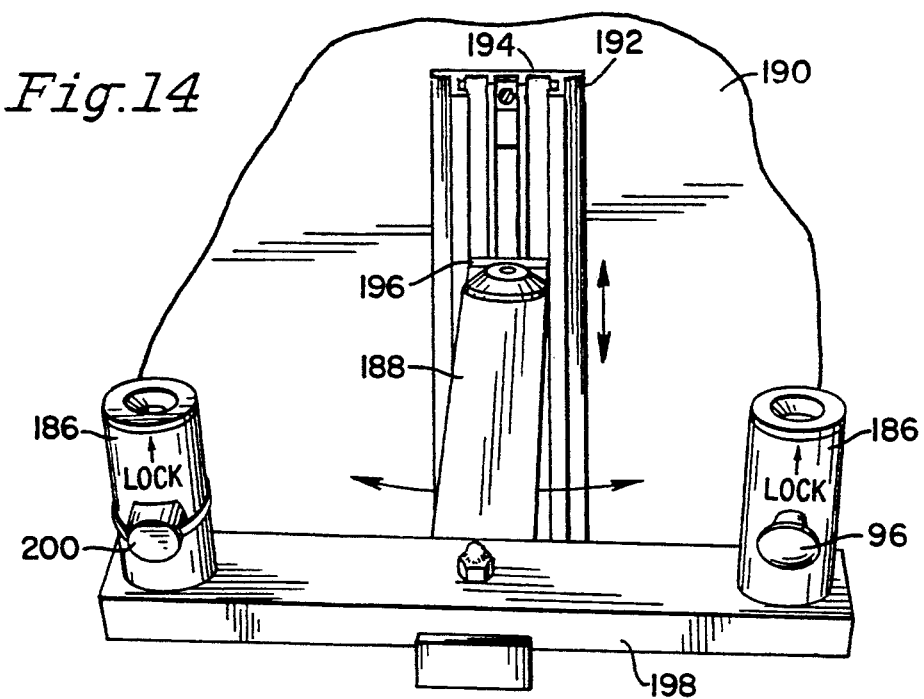
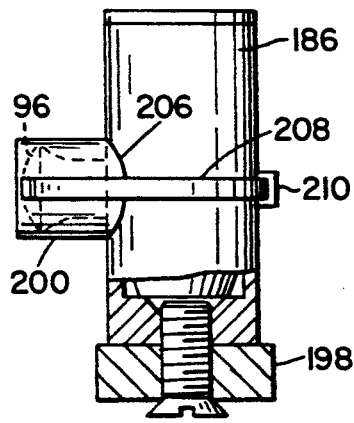
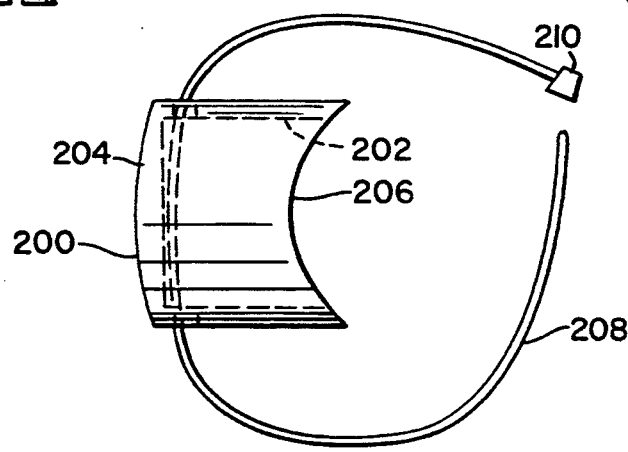
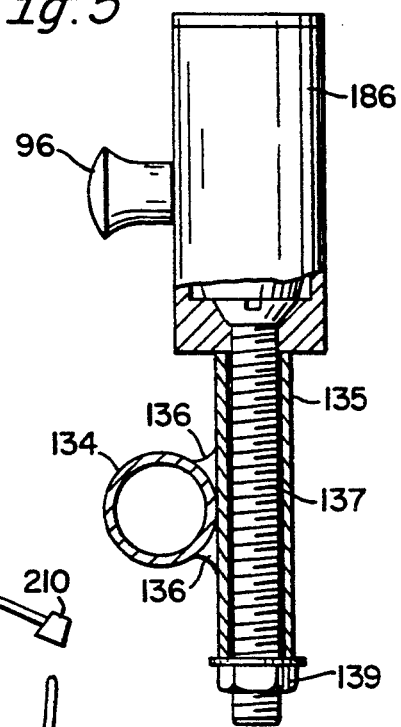

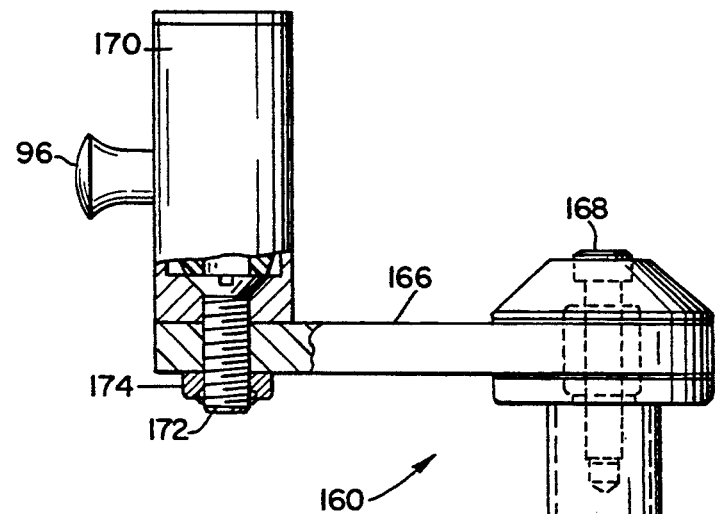
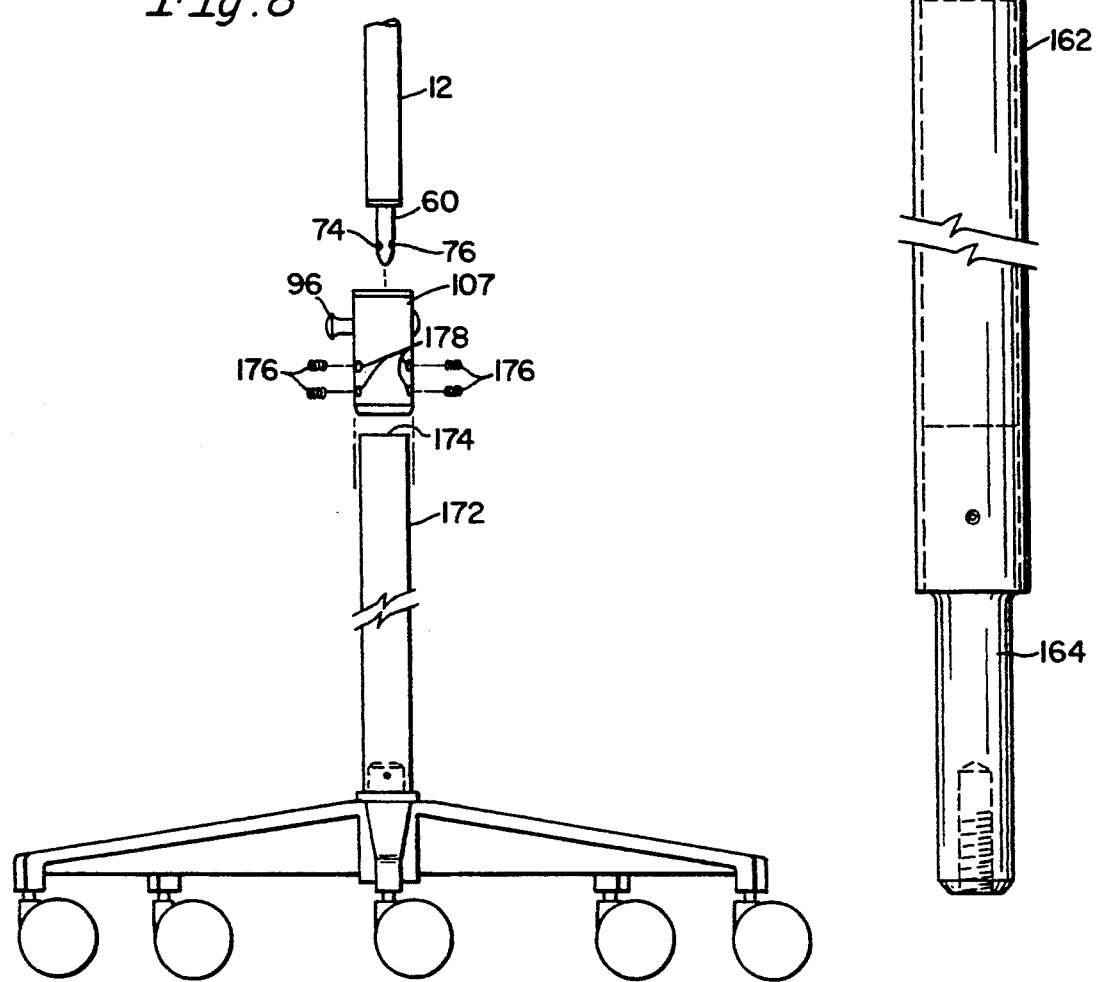

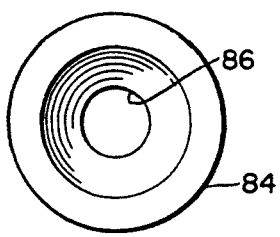
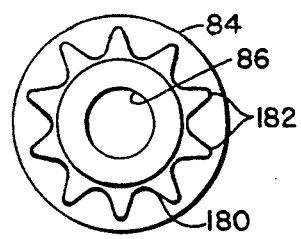
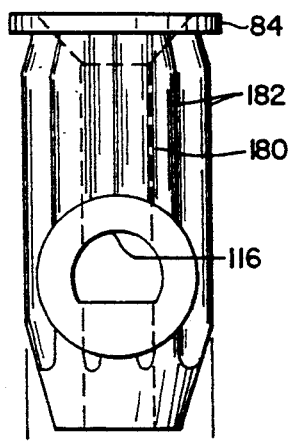
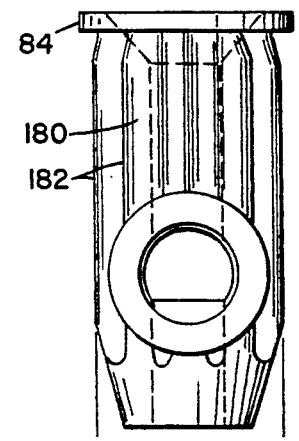
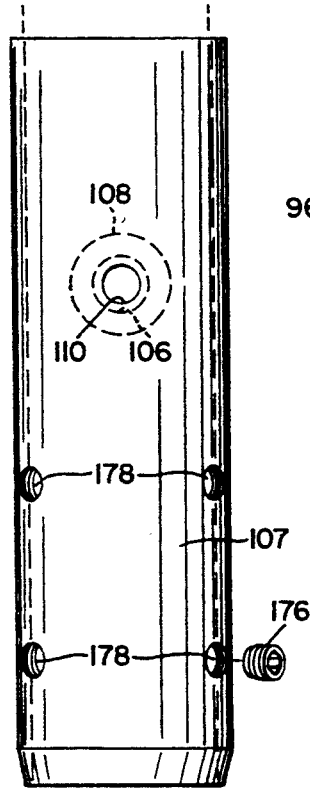
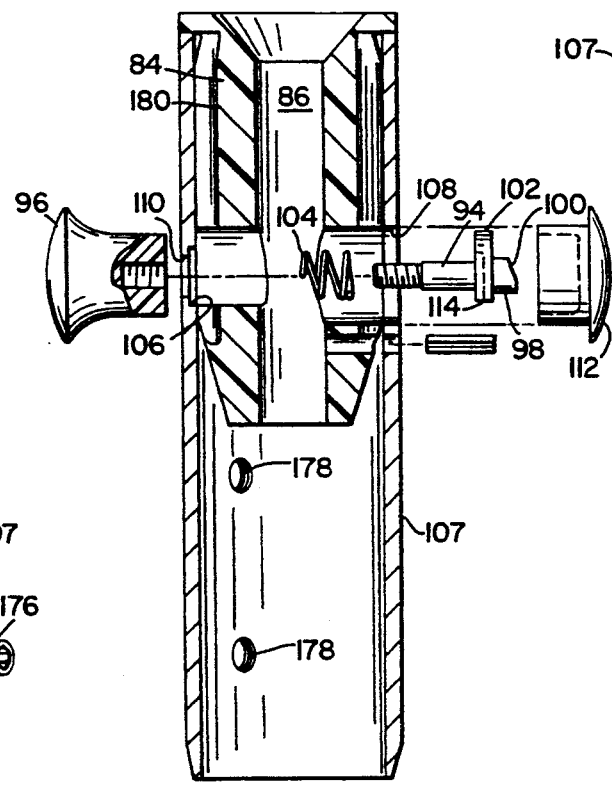
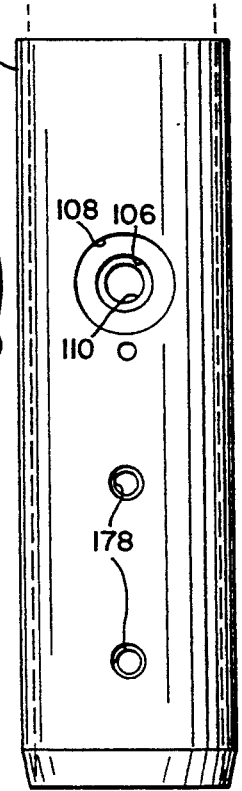

SUPPORT APPARATUS FOR A PATIENT INFUSION DEVICE

BACKGROUND OF THE INVENTION

1. Field of the Invention

The present invention relates to support apparatus for selectively connecting a medical patient infusion device, such as an infusion bag or an infusion pump, either to an infusion device mobile support, to a bed, to a stretcher, or to a wheelchair that is used to transport a patient. More particularly, the present invention relates to an infusion device support that includes a support connector that is capable of releasable yet locked connection with a complementary support receptacle that is carried on either the transporter, the stretcher, the bed, or the wheelchair.

2. Description of the Related Art

Medical patients receiving either medication or nutrition, or both, from a liquid-containing infusion device, such as an infusion bag or an infusion pump, frequently must be transported from one place to another within a hospital or other medical care facility. In the past it was necessary that at least one person be provided to safely move the patient, while the patient was resting either in a wheelchair or on a mobile stretcher, and then to provide another person for safely moving the infusion device stand while the infusion device remained connected with the patient. The need to employ two persons to move a patient connected with an infusion device requires additional personnel that results in excessive additional costs. With the current emphasis on reduction of the costs of medical care, a less costly and more efficient method is highly desirable.

One way in which the additional person can be eliminated while transporting a patient is to provide an intravenous equipment support of the type disclosed in U.S. Pat. No. 4,725,027, which issued on Feb. 16, 1988, to the present inventor. That patent discloses a separable intravenous equipment support stand in which the upper portion of the stand can be separated from the lower portion of the stand and connected with a receptacle carried by a stretcher or other means of patient transport. Although the structural arrangement disclosed in that patient is eminently suitable for the disclosed purpose, it is desirable to make that apparatus more easily usable.

It is an object of the present invention to provide improved support apparatus for a patient infusion device.

It is another object of the present invention to provide support apparatus that permits convenient transfer and secure retention of an infusion device holder from one type of patient support or carrier to another, while the infusion device remains connected with the patient.

SUMMARY OF THE INVENTION

Briefly stated, and in accordance with one aspect of the present invention, apparatus is provided for carrying a patient infusion device, such as an intravenous-fluid-containing flexible bag or a rigid infusion pump holder, and for releasable connection of the apparatus with an infusion device support in the form of a receptacle carried on a stationary or a movable support. The apparatus includes an infusion device carrier including a support bar for supporting an infusion device, the support bar having an end defining a support connector adapted for releasable connection with a support receptacle. The support connector includes a coupling rod that extends from the support bar and terminates in a conical end that defines a conical camming surface. The coupling rod includes a longitudinal axis and a pair of opposed recesses, each recess extending transversely at the coupling rod longitudinal axis for receiving a transversely shiftable detent.

A support receptacle is provided for releasably receiving the coupling rod and supporting the support connector. The support receptacle includes a bore for slidably receiving the coupling rod, the bore having a longitudinal axis adapted to be coaxially aligned with the longitudinal axis of the coupling rod. The receptacle includes a detent carried for transverse movement toward and away from the support receptacle longitudinal axis, the detent being spring biased toward the support receptacle longitudinal axis and having an end including a camming face inclined relative to the support receptacle longitudinal axis for engagement with the conical camming surface of the coupling rod. The detent end is receivable within one of the recesses in the coupling rod to prevent relative axial and rotational movement of the coupling rod and the support receptacle bore for locking the coupling rod in position within the support receptacle.

BRIEF DESCRIPTION OF THE DRAWINGS

FIG. 2 is an enlarged, fragmentary, cross-sectional view showing a support connector in accordance with the present invention together with an adapter member for securing the support connector with a flange carried on a tubular frame member.

FIG. 3 is a fragmentary elevational view of a support connector in accordance with the present invention engaged with a support receptacle and showing alignment indicia for facilitating proper alignment of the connector and receptacle.

FIG. 4 is a fragmentary elevational view similar to FIG. 3 showing the connector and support of FIG. 3 rotated 90° relative to each other.

FIG. 5 is a cross-sectional view similar to that of FIG. 2, partially in section, showing another form of connection of a support receptacle in accordance with the present invention with a tubular horizontal frame member. FIG. 6 is a fragmentary perspective view showing a support connector and support receptacle in accordance with the present invention arranged for use with a wheelchair.

FIG. 7 is an enlarged elevational view, partially broken away, showing a support receptacle in accordance with the present invention for mounting the receptacle on a bed mount.

FIG. 8 is an exploded view of a lower portion of an infusion device transport stand showing an adapter for conversion of an existing stand for use with a support connector and support receptacle in accordance with the present invention.

FIG. 9 is an enlarged longitudinal sectional view of the support receptacle shown in FIG. 8, also showing the parts of a transversely movable detent in exploded form.

FIG. 10 is a left side view of the support receptacle of FIG. 9 with the inner sleeve removed from the outer sleeve and without the detent structure.

FIG. 11 is a view similar to FIG. 10, showing the right side of the support receptacle of FIG. 9.

FIG. 12 is a top view of the adapter inner sleeve shown in FIG. 9.

FIG. 13 is a bottom view of the adapter inner sleeve shown in FIG. 9.

FIG. 14 is a fragmentary perspective view showing a dual support receptacle holder coupled with a wall mount.

FIG. 15 is an enlarged side view, partially broken away, showing the mounting of a support receptacle to the support bar shown in FIG. 14.

FIG. 16 is a top view of a cover cap and associated fastening strap for covering the detent operating knob.

DESCRIPTION OF THE PREFERRED EMBODIMENTS

Figure 1:
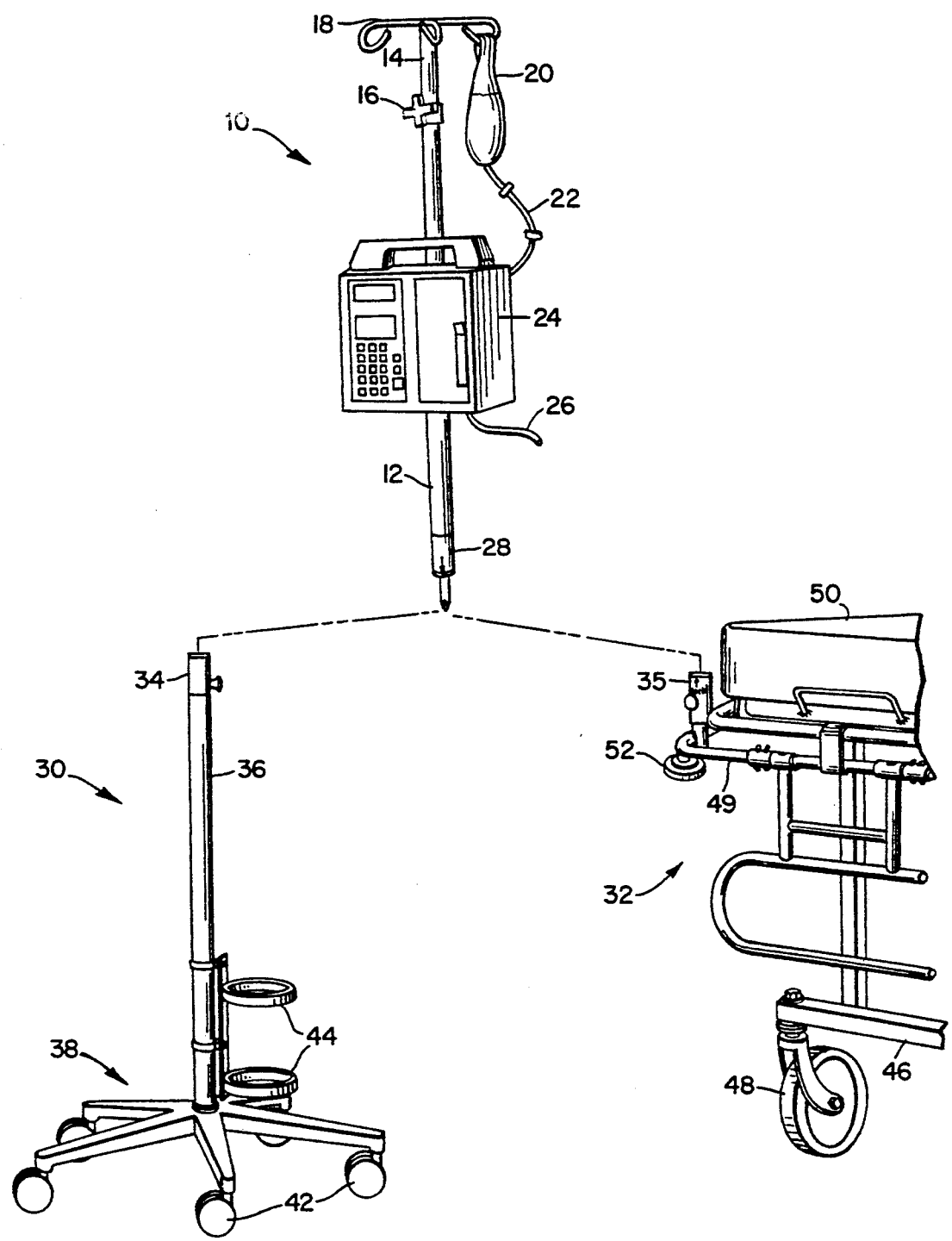
FIG. 1 is an elevational, perspective view of a support apparatus for a patient infusion device in accordance with the present invention shown together with a base of a transport stand and also with a portion of a mobile stretcher.

Referring now to the drawings, and particularly to FIG. 1 thereof, there is shown an infusion device support 10 including a main support bar 12 of generally tubular configuration. Extending from the upper end of main support bar 12 is an upper support bar 14 that is telescopically received within main support bar 12 and is held in a desired position relative thereto by means of a screw-type clamp 16 of conventional form.

Connected to the uppermost end of upper support bar 14 is a hanger 18 for supporting a fluid container 20, such as a flexible bag containing an infusion liquid. Container 20 is mounted in inverted position and includes an outlet tube 22 that is connected an infusion flow control device 24, such as an infusion pump as illustrated generally in FIG. 1. Extending from infusion flow control device 24 is an intravenous tube 26 that carries the infusion liquid to the patient. Because the infusion flow control device is of known construction, and because the structure and operation of such devices are familiar to those skilled in the art they will not be further described herein.

At the lower end of main support bar 12, the end opposite from the end from which upper support bar 14 extends, is a support connector 28 that defines an upper coupling member for coupling main support bar 12 with an infusion device support stand 30, or with a patient support device such as the mobile stretcher 32 shown in fragmentary form in FIG. 1. Each of infusion device support stand 30 and mobile stretcher 32 includes a support receptacle 34, 35, respectively, that defines a lower coupling member that is engagable with support connector 28, or upper coupling member, as will be hereinafter described in greater detail.

Support stand 30 includes a lower support bar 36 extending upwardly from a base 38 defined by a plurality of outwardly extending legs 40 each carrying a swivel caster 42. Support receptacle 34 is secured to the uppermost end of lower support bar 36. If desired, lower support bar 36 can also support an oxygen cylinder holder 44, as shown in FIG. 1.

Mobile stretcher 32 includes a base frame 46 having a plurality of wheels 48, only one of which is shown, and a rectangular, horizontally disposed tubular support frame 49 that supports a mattress 50. Each corner of support frame 49 carries a resilient bumper 52, and adjacent to at least one of bumpers 52 and secured to support frame 49 is a support receptacle 35 having the same structure as support receptacle 34 carried by support stand 30.

As shown in FIG. 1, main support bar 12 can be connected to infusion device support stand 30 by interconnecting support connector 28 with support receptacle 34. Alternatively, main support 12 bar can be connected to mobile stretcher 32 by interconnecting support connector 28 with support receptacle 35 carried by support frame 49. As will be appreciated, the structure illustrated and described herein permits infusion flow control device 24 to be selectively shifted from support stand 30 to mobile stretcher 32 and back again, as desired. Consequently, when a patient is being transported on stretcher 32 it is unnecessary to provide an additional person to push support stand 30 alongside stretcher 32 in order to maintain constant and uninterrupted flow of the infusion fluid into the patient as he or she is being transported.

The internal structure of each of support connector 28 and support receptacle 35, constituting the upper and lower coupling members, respectively, is best seen in FIG. 2, which shows the coupling members interconnected and in locked relationship to securely connect main support bar 12 with support frame 49 of mobile stretcher 32. As shown, main support bar 12 is of tubular form and has positioned within its lowermost end an inner tubular sleeve 54 that preferably fits snugly within the lowermost end of support bar 12, and which is secured thereto by means of a transversely extending pin 56, such as a roll pin, a dowel pin, or the like, to provide a secure interconnection between inner tubular sleeve 54 and upper support bar 12. Inner tubular sleeve 54 includes a centrally positioned inner bore 58 that receives a coupling rod 60, which is also held in position within tubular sleeve 54 by pin 56. The lowermost end of tubular sleeve 54 includes a transversely extending flange 62 that is preferably of the same outer diameter as that of support bar 12, and that defines a support connector engagement surface 64.

Coupling rod 60 is a cylindrical member having an inner end 66 that is received against an inwardly extending shoulder 68 formed in bore 58 of tubular sleeve 54. Coupling rod 60 includes an outer end 70 that is of conical form, and that defines a conical camming surface 72 that is symmetrical about the longitudinal axis of coupling rod 60. A pair of diametrically opposed, transversely extending recesses 74, 76 are provided in coupling rod 60 immediately adjacent conical camming surface 72. As illustrated in FIG. 2, recesses 74 and 76 are defined by a transversely extending throughbore 78 that passes completely through coupling rod 60 and intersects the longitudinal axis of rod 60.

Support receptacle 35 includes an outer sleeve 80 that can be an elongated tubular member similar to lower support bar 36 forming part of infusion device support stand 30. Alternatively, outer sleeve 80 can be of limited axial length to define an adapter outer sleeve that can be telescopically connected with and secured to a cylindrical mounting structure such as the cylindrical base member 82 shown in FIG. 2. Outer sleeve 80 includes an inner sleeve 84 that has an overall structure similar to that of inner sleeve 54 of support connector 28, in that it includes a central bore 86 and an outwardly extending flange 88 that defines a support receptacle engagement surface 90. Bore 86 has an inner diameter that corresponds with the outer diameter of coupling rod 60 in order to slidably receive the coupling rod and to provide lateral support to the rod and the associated structure of main support bar 12. Inner sleeve 84 is secured to outer sleeve 80 by a transversely extending pin 92, which can be a roll bar or the like, as was described above in connection with support connector 28.

A transversely extending locking pin 94 is carried within both outer sleeve 80 and inner sleeve 84 for engagement with recess 74 in coupling rod 60. Locking pin 94 has an outer end to which a release knob 96 is connected, and has an inner end that terminates in a detent 98 having a camming face 100 that is inclined relative to the longitudinal axis of locking pin 94 and is also inclined relative to the longitudinal axis of inner sleeve 84. Locking pin 94 carries a transversely extending stop flange 102 that is positioned between the inner and outer ends of pin 94 and is spaced from camming face 100 a sufficient distance to provide a cylindrical surface that is received within one of recesses 74, 76 formed in coupling rod 60. A coil spring 104 is provided in surrounding relationship with locking pin 94 and is positioned between stop flange 102 and a spotface 106 formed on the inner surface of outer sleeve 80.

The structural details of locking pin 94 are shown in FIG. 9 in an exploded view. As also shown in FIG. 9, another form of tubular outer sleeve 107, which is generally similar in overall structure to outer sleeve 80, includes a transversely positioned opening 108 that is diametrically opposite a lock pin aperture 110. Opening 108 is of sufficient diameter to permit assembly of the several locking pin elements within each of inner sleeve 84 and outer sleeve 107. A plastic sealing plug 112, or the like, is provided to close opening 108 after the several parts of the locking pin arrangement have been assembled within the support receptacle.

The locking pin stop flange 102 is preferably of generally circular overall form and includes a flattened edge 114 so that it is non-rotatably received within a correspondingly-shaped stop flange opening 116 formed in inner sleeve 84 (see FIG. 10).

Referring once again to FIG. 2, outer sleeve 80 is secured to cylindrical base member 82 by means of a roll pin 118, or the like, that is received in a transverse bore 120 formed in base member 82. Roll pin 118 has a length sufficient to permit it to extend into a pair of diametrically opposed apertures 122, 124 formed in outer sleeve 80. Base member 82 includes an annular stop flange 126 on which the lower end of outer sleeve 80 rests. A blind threaded bore 128 is provided in the downwardly facing end of base member 82 to permit attachment of base member 82 to a flange 130 or other structure by means of a connecting bolt 132. As illustrated in FIG. 2, flange 130 is secured to a tubular horizontal frame member 134, such as by means of welds 136. Frame member 134 can form part of a mobile stretcher, having a structure as illustrated generally in FIG. 1, or it can be a part of the frame of a wheelchair, or the like.

An alternative connection arrangement for connecting a receptacle with a tubular frame member is shown in FIG. 5. A vertically extending sleeve 135 is welded to frame member 134 by means of welds 136. Support receptacle 186 is secured to the structure by bolt 137 that extends through the base of receptacle 186 and sleeve 135 and to which nut 139 is threadedly connected to bear against the lower end of sleeve 135.

As best seen in FIGS. 3 and 4, support connector 28 and support receptacle 35 each include alignment indicia 138, 140, respectively, for facilitating alignment of one of recesses 74, 76 in coupling rod 60 with the axis of locking pin 94 carried in support receptacle 35. In that regard, alignment indicia 140 on support receptacle 35 includes an axially extending arrow, or the like, together with the legend "lock." The arrow is so positioned that if extended it intersects the longitudinal axis of locking pin 94.

Alignment indicia 138 on support connector 28 can also include an orientation arrow together with the legend "lock," which appears on support connector 28 at two positions that are spaced 180° apart. In each instance the arrows constituting alignment indicia 138, if extended, would intersect the axes of recesses 74, 76 in coupling rod 60.

In addition to the arrows forming part of alignment indicia 138, only one of which is shown in FIG. 3, offset 90 degrees from each of the "lock" legends on support connector 28 are a pair of "unlock" legends along with a circumferentially extending, double headed arrow. Thus, when the lock arrow of support receptacle 35 is aligned with the lock arrow of support connector 28, the longitudinal axis of locking pin 94 will coincide with the axis of each of recesses 74 and 76 in coupling rod 60 when coupling rod 60 has been positioned at the proper depth within inner sleeve 84. If the respective lock arrows on each of support coupling 28 and support receptacle 35 are not aligned, the device is not in locked condition, and the unlock arrows, one of which would in any event be adjacent the lock arrow on support receptacle 35, would indicate that support connector 28 must be rotated in either direction in order to effect proper alignment of locking pin 94 and either of recesses 74 or 76.

In operation, support connector 28 and support receptacle 34 or 35 are interconnected by inserting coupling rod 60 into inner sleeve bore 86 until engagement surfaces 64 and 90 of the respective inner sleeves 54 and 84 are in contact. As will be apparent from reference to FIG. 2, the downward movement of coupling rod 60 causes conical camming surface 72 to contact inclined camming face 100 on locking pin 94 and urges locking pin 94 outwardly so that detent release knob 96 is moved outwardly away from outer sleeve 80. If the respective lock arrows of the alignment indicia 138, 140 of each of support connector 28 and support receptacle 35 are aligned, locking pin 94 will be moved outwardly until one of recesses 74, 76 is aligned with detent 98, whereupon the detent is urged into the recess by biasing spring 104 acting against annular stop flange 102. As a result, detent 98 is received within coupling rod 60 to hold the support receptacle and support coupling together to prevent both unintended relative rotation and unintended axial separation thereof.

If coupling rod 60 is inserted into bore 86 in inner sleeve 84 and the respective alignment indicia 138, 140 in the form of lock arrows on support connector 28 and on support receptacle 35 are not in alignment, which is the condition illustrated in FIG. 4, engagement surfaces 64 and 90 will come into contact with each other without the connector and receptacle being locked together. In that instance, camming face 72 will urge locking pin 94 outwardly, but detent 98 will not be received within one of recesses 74, 76. Proper alignment of the detent and a recess can be effected by rotating support connector 28 relative to support receptacle 35 until the respective lock arrows are in alignment, at which point the locking pin axis and the axes of the respective recesses will also be in alignment, thereby permitting detent 98 to snap into one of recesses 74 or 76 by virtue of spring 104 to securely engage coupling rod 60 and thereby lock support connector 28 and support receptacle 35 together.

Although shown in FIG. 2 as including an outer sleeve 80 connected with a base member 82 through a connecting pin 118, a support receptacle can be provided as an integral part of a frame structure as illustrated in FIG. 6. As there shown, a wheelchair 140 includes an arm frame member 142, an arm 144, and a back frame member 146 that supports a flexible back panel 147 and includes a push handle 148. Extending upwardly along the back of wheelchair 140 is an upwardly-extending support member 150 that includes at its uppermost end a support receptacle 152 in accordance with the present invention. Support member 150 corresponds structurally with outer sleeve 80 shown in FIG. 2, and includes an inner sleeve 84 that terminates in an annular engagement surface 90, and a central bore for receiving coupling rod 60 of support connector 28.

In the orientation of the parts as shown in FIG. 6, the alignment arrows constituting the alignment indicia 138, 140 on each of support connector 28 and support receptacle 152, respectively, are in alignment. Consequently, recess 74 in coupling rod 60 has its axis aligned with the axis of the locking pin (not shown) carried by support receptacle 152, so that when the engagement surfaces 64 and 90 of each of support connector 28 and support receptacle 152 are brought into contact the detent is received in the recess to securely lock together the support connector with the support receptacle. A patient sitting in the wheelchair can then be pushed by only one attendant, with the infusion device connected with and supported by the wheelchair, and without the need for another person to separately push an infusion device support stand and follow along with the wheelchair.

The support connector structure in accordance with the present invention can also be employed to connect with a bed frame that has an upwardly opening tubular sleeve (not shown) to receive a holder 160 having the structure illustrated in FIG. 7. A support rod 162 includes an engagement rod 164 that is received in a bed frame. Support rod 162 serves to elevate an infusion device relative to a patient resting in the bed. An offset plate member 166 is secured to the upper end of rod 162 by means of a bolt 168, or the like, to permit the outer end of plate member 166 to be positioned at any of a number of positions spaced radially outwardly of the axis of support rod 162 and of the bed frame opening in which holder 160 is received. A support receptacle 170 having an inner sleeve 84 and a detent 72 corresponding with the structure illustrated and described in FIGS. 2 and 9 is secured to the outer end of offset support plate 166 by means of a connecting bolt 172 and nut 174. An infusion device holder, such as main support bar 12 shown in FIG. 1 incorporating a support connector 28, can thus be connected with and secured to holder 160 and can be oriented in any convenient position by rotating support rod 162 with the associated bed frame support. Again, an infusion flow control device 24 as shown in FIG. 1 can be connected with a bed in the same manner as has been described hereinabove with respect to the structures illustrated in FIGS. 3, 4, and 6.

A support receptacle in accordance with the present invention can also be provided in the form of a conversion unit for adapting the connector herein disclosed with existing tubular members, such as existing infusion device support stands. Referring now to FIG. 8, there is shown the base portion of a common form of infusion device support stand that includes an upwardly extending support tube 172. To permit such an existing stand to accommodate the support arrangement in accordance with the present invention, the upper portion of support tube 172 is sawed off, as at 174, and an adapter outer sleeve 107 as shown in FIGS. 9 through 11 is provided to fit slidably over the free upper end of support tube 172 as illustrated in FIG. 8. Outer sleeve 107 is secured to support tube 172 by a plurality of radially extending setscrews that are received in respective radially extending threaded bores 178 in outer sleeve 107.

The elements of such a conversion unit are shown in enlarged form in FIGS. 9 through 13. As shown in FIGS. 10, 11, and 13, outer surface 180 of inner sleeve 84 is preferably formed to include a plurality of circumferentially positioned ridges 182 to engage with the inner surface of outer sleeve 107, and to permit displacement of material at the inner surface of outer sleeve 107, as necessary, to effect a tight and secure interconnection between inner sleeve 84 and outer sleeve 107.

In addition to the ability to use the present invention with movable devices, such as infusion device support stands, mobile stretchers, wheelchairs, and beds, the present invention can also be utilized in connection with fixed structures. Referring now to FIG. 14, there is shown a wall mount arrangement whereby a pair of support receptacles 186 in accordance with the present invention are carried on a support arm 188 that is supported from a wall 190. A vertically extending extruded member 192 defines a vertical track 194 that has a cross section adapted to slidably receive a guide member 196 that can be clamped in a desired position along track 194 in a manner well known to those skilled in the art. Guide member 196 pivotally supports arm 188, and the outermost end of arm 188 is, in turn, bolted to a transversely extending support bar 198, each end of which carries a support receptacle 186 in accordance with the present invention. The disclosed structure permits arm 188 to be moved along track 194 to a desired position, and also permits arm 188 to be pivoted about guide member 196. Thus, the dual holder wall mount illustrated permits a pair of infusion device supports to be carried on the support bar to provide a bedridden patient with multiple infusion fluids, if necessary.

A support connector carried by an infusion device support 10 as shown in FIG. 1 can be disconnected from an associated support receptacle 186 by pulling outwardly on the detent release knob 196. The detent is thereby withdrawn from the recess in the coupling rod carried by the support connector of support 10, thus permitting withdrawal of the coupling rod from support receptacle 186. In order to prevent unintended separation of a support connector from an associated support receptacle, a cover cap 200 can be provided to overlie and cover detent release knob 96 and prevent its unintended actuation. Cover cap 200 is shown in position over a detent release knob 96 in FIGS. 14 and 15, and is shown in enlarged form in FIG. 16.

Cover cap 200 defines an inner chamber 202 that is of sufficient size to completely enclose detent release knob 96. Cap 200 includes a closed end 204 to overlie detent release knob 96, and the open end of the cap has a curved surface 206 that has a curvature adapted to engage with the outer cylindrical surface of support receptacle 186. A connecting strap 208 extends from opposite sides of cap 200 and includes a cinch 210 or grip at one end thereof for receiving and tightly engaging the other, free end of strap 208 to permit cover cap 200 to be secured in position about support receptacle 186. Preferably, cover cap 200 is made from plastic material, such as high density polyethylene, polypropylene, or the like.

It will be apparent that the present invention provides distinct advantages over the prior art structures in that it permits convenient and rapid connection and disconnection of an infusion flow control device with a transport stand, or with a patient transport device such as a mobile stretcher, a wheelchair, or a bed, as well as with stationary structural elements such as a wall. Additionally, the present invention permits interconnection of the support connector and the support receptacle and locking in either of two orientations that are 180° apart.

Although particular embodiments of the present invention have been illustrated and described, it will be apparent to those skilled in the art that various changes and modifications can be made without departing from the spirit of the present invention. It is therefore intended to encompass within the appended claims all such changes and modifications that fall within the scope of the present invention.

What is claimed is:

1. Apparatus for carrying a patient infusion device, such as an intravenous-fluid-carrying bag or an infusion pump, and for releasable connection of the infusion device with an infusion device support carried by a stationary or a movable receptacle, said apparatus comprising:

a. an infusion device carrier including a support bar for supporting an infusion device, the support bar having an end defining a support connector adapted for releasable connection with a support receptacle, the support connector including a coupling rod extending from the support bar and terminating in a conical end that defines a conical camming surface, the coupling rod including a longitudinal axis and a pair of opposed recesses, each recesses having an axis extending transversely of the coupling rod longitudinal axis for receiving a transversely shiftable detent rod; and b. a support receptacle for receiving the coupling rod and supporting the support connector, the support receptacle including a tubular sleeve having a bore for slidably receiving the coupling rod, the bore having a longitudinal axis adapted to be coaxially aligned with the longitudinal axis of the coupling rod, said sleeve having a pair of coaxial transverse bores, a detent rod carried by the support receptacle for slidable transverse movement within one of said transverse bores toward and away from the support receptacle longitudinal axis, the detent rod being spring biased toward the support receptacle longitudinal axis and having an end including a camming face inclined relative to the support receptacle longitudinal axis for engagement with the conical camming surface of the coupling rod, the detent end being receivable within one of the recess in the coupling rod for preventing relative axial and rotational movement of the support connector and the support receptacle for locking the coupling rod in position within the support receptacle bore, the other of said coaxial transverse bores being larger than said one transverse bore to facilitate assembly of said detent rod in said one transverse bore.

2. Apparatus in accordance with claim 1, wherein the support connector and the support receptacle each carry a respective pair of alignment indicia on oppositely facing surfaces thereof for facilitating alignment of the detent with one of the coupling rod recesses to permit rapid engagement of the detent with one of the coupling rod recesses to lock the support connector to the support receptacle.

3. Apparatus in accordance with claim 2, wherein the support connector and the support receptacle each include respective transverse engagement surfaces for limiting inward movement of the coupling rod into the support receptacle bore, and the alignment indicia are each positioned adjacent the transverse engagement surfaces and include a pair of longitudinally oriented primary indicia that are radially aligned with respective one of the coupling rod recess and the detent rod axis.

4. Apparatus in accordance with claim 1, wherein the support connector includes secondary indicia to indicate nonalignment of the coupling rod recesses and the detent axis and to indicate relative rotation to enable alignment to be accomplished.

5. Apparatus in accordance with claim 1, wherein the opposed recesses in the coupling rod are defined by a transversely extending through bore.

6. Apparatus in accordance with claim 1, wherein the support receptacle is adapted to be carried by a wheelchair frame member.

7. Apparatus in accordance with claim 1, wherein the support receptacle includes an adapter sleeve, and the sleeve includes mounting means for mounting the sleeve to a support member.

8. Apparatus in accordance with claim 7, wherein the mounting means includes a plurality of threaded apertures in the adapter sleeve for threadedly receiving setscrews for engagement with an outer surface of the support member.

9. Apparatus in accordance with claim 1, wherein the support receptacle is adapted to be supported on a bed frame.

10. Apparatus in accordance with claim 9, wherein the support receptacle is mounted on an offset arm carried by a holder receivable by the bed frame.

11. Apparatus in accordance with claim 1, comprising a wall mount, the support receptacle being supported from said wall mount.

12. Apparatus in accordance with claim 11, wherein the wall mount includes a dual mount for simultaneously carrying a pair of support receptacles.

13. Apparatus in accordance with claim 11, wherein the wall mount includes a track member for slidably supporting a guide member, and wherein the support receptacle is connected to the guide member.

14. Apparatus in accordance with claim 13, wherein the guide member carries an arm that supports a pair of spaced support receptacles.

15. Apparatus in accordance with claim 14, wherein the arm is pivotally carried by the guide member.

16. Apparatus in accordance with claim 1, wherein the detent includes a detent knob that extends outwardly from the support receptacle, and further including a removable cover cap adapted to cover the detent knob for preventing unintended actuation of the detent knob.

17. Apparatus for carrying a patient infusion device, such as an intravenous-fluid-carrying bag or an infusion pump, and for releasable connection of the infusion device with an infusion device support carried by a stationary or a movable receptacle, said apparatus comprising:
- a. an infusion device carrier including a support bar for supporting an infusion device, the support bar having an end defining a support connector adapted for releasable connection with a support receptacle, the support connector including a coupling rod extending from the support bar and terminating in an end that defines a camming surface, the coupling rod including a longitudinal axis and a pair of opposed recesses, each recess having an axis extending transversely of the coupling rod longitudinal axis for receiving a transversely shiftable detent rod; and
- b. a support receptacle for releasably receiving the coupling rod and supporting the support connector, the support receptacle including a tubular sleeve having a bore for slidably receiving the coupling rod, the bore having a longitudinal axis adapted to be coaxially aligned with the longitudinal axis of the coupling rod, said sleeve having a pair of coaxial transverse bores, a detent rod carried by the support receptacle for slidable transverse movement within one of said transverse bores toward and away from the support receptacle longitudinal axis, the detent rod being spring biased toward the support receptacle longitudinal axis and having an end including a camming face for engagement with the camming surface of the coupling rod, the detent end being receivable within one of the recesses in the coupling rod for preventing relative axial and rotational movement of the support connector and the support receptacle for locking the coupling rod in position within the support receptacle bore, the other of said coaxial transverse bores being larger than said one transverse bore to facilitate assembly of said detent rod in said one transverse bore.

18. Apparatus in accordance with claim 17, comprising a plug closing said other transverse bore.

19. Apparatus in accordance with claim 17, wherein the support receptacle includes an adapter sleeve, and the sleeve includes mounting means for mounting the sleeve to a support member.

20. Apparatus in accordance with claim 19, wherein the mounting means includes a plurality of threaded apertures in the adapter sleeve for threadedly receiving setscrews for engagement with an outer surface of the support member.

* * * * *